United States Patent [19]
Berg et al.

[11] Patent Number: 4,597,834
[45] Date of Patent: * Jul. 1, 1986

[54] SEPARATION OF METHYL ACETATE FROM METHANOL BY EXTRACTIVE DISTILLATION

[76] Inventors: Lloyd Berg; An-I Yeh, both of 1314 S. Third Ave., both of Bozeman, Mont. 59715

[*] Notice: The portion of the term of this patent subsequent to Apr. 5, 2000 has been disclaimed.

[21] Appl. No.: 581,344

[22] Filed: Feb. 17, 1984

Related U.S. Application Data

[62] Division of Ser. No. 485,006, Apr. 14, 1983, Pat. No. 4,543,164.

[51] Int. Cl.$^4$ .................... B01D 3/40; C07C 67/48
[52] U.S. Cl. ........................................ 203/51; 203/56; 203/57; 203/58; 203/60; 203/64; 560/248
[58] Field of Search .................. 560/248; 568/913; 203/51, 56, 57, 58, 60, 64

[56] References Cited

U.S. PATENT DOCUMENTS

| 3,268,572 | 8/1966 | Knörr et al. | 203/60 |
| 3,431,181 | 3/1969 | Bouniot | 203/60 |
| 3,709,928 | 1/1973 | Murayama et al. | 203/64 |
| 4,379,028 | 4/1983 | Berg et al. | 560/248 |
| 4,431,838 | 2/1984 | Feldman et al. | 560/248 |

FOREIGN PATENT DOCUMENTS

| 1088040 | 9/1960 | Fed. Rep. of Germany | 203/64 |
| 1089744 | 9/1960 | Fed. Rep. of Germany | 203/64 |
| 3135280 | 3/1983 | Fed. Rep. of Germany | 560/248 |
| 119411 | 9/1979 | Japan | 203/64 |
| 967471 | 8/1964 | United Kingdom | 203/60 |
| 642295 | 1/1979 | U.S.S.R. | 203/56 |

Primary Examiner—Wilbur Bascomb

[57] ABSTRACT

Methyl acetate cannot be completely removed from methyl acetate - methanol mixtures by distillation because of the presence of the minimum binary azeotrope. Methyl acetate can be readily removed from mixtures containing it and methanol by using extractive distillation in which the extractive distillation agent is a higher boiling oxygenated, nitrogenous and/or sulfur containing organic compound or a mixture of these. Typical examples of effective agents are dimethylformamide; dimethylsulfoxide plus tetraethylene glycol, dimethylsulfoxide plus 1,5-pentanediol plus 1,6-hexanediol.

2 Claims, No Drawings

SEPARATION OF METHYL ACETATE FROM METHANOL BY EXTRACTIVE DISTILLATION

This application is a divisional of application Ser. No. 06/485,006 filed Apr. 14, 1983 now U.S. Pat. No. 4,543,164.

FIELD OF THE INVENTION

This invention relates to a method for separating methyl acetate from methanol using certain higher boiling liquids as the extractive agent in extractive distillation.

DESCRIPTION OF PRIOR ART

Extractive distillation is the method of separating close boiling compounds or azeotropes by carrying out the distillation in a multiplate rectification column in the presence of an added liquid or liquid mixture, said liquid(s) having a boiling point higher than the compounds being separated. The extractive agent is introduced near the top of the column and flows downward until it reaches the stillpot or reboiler. Its presence on each plate of the rectification column alters the relative volatility of the close boiling compounds in a direction to make the separation on each plate greater and thus require either fewer plates to effect the same separation or make possible a greater degree of separation with the same number of plates. When the compounds to be separated normally form an azeotrope, the proper agents will cause them to boil separately during extractive distillation and thus make possible a separation in a rectification column that cannot be done at all when no agent is present. The extractive agent should boil higher than any of the close boiling liquids being separated and not form minimum azeotropes with them. Usually the extractive agent is introduced a few plates from the top of the column to insure that none of the extractive agent is carried over with the lowest boiling component. This usually requires that the extractive agent boil twenty Centigrade degrees or more higher than the lowest boiling component.

At the bottom of a continuous column, the less volatile components of the close boiling mixtures and the extractive agent are continuously removed from the column. The usual methods of separation of these two components are the use of another rectification column, cooling and phase separation, or solvent extraction.

One of the commercially important ways to manufacture methyl acetate is by the catalytic esterification of methanol with acetic acid. Methyl acetate, (b.p.=56.3° C.) and methanol, (b.p.=64.5° C.) form a binary azeotrope boiling at 54° C. and containing 81.3 weight percent methyl acetate, 18.7 wt.% methanol. Methyl acetate also forms a binary azeotrope with water which boils at 56.1° C. and contains 95 wt.% methyl acetate. Methyl acetate, methanol and water do not form a ternary azeotrope. Thus in the esterification of methanol with acetic acid to form methyl acetate and water, the rectification of this mixture yields the lowest boiling constituent, namely the methyl acetate-methanol azeotrope. It is therefore impossible to produce methyl acetate from methanol mixtures by rectification because the lower boiling azeotrope will always come off overhead as the initial product. Any mixture of methyl acetate and methanol subjected to rectification at one atmosphere pressure will produce an overhead product boiling at 54.0° C. and containing 81.3 wt.% methyl acetate, 18.7 wt.% methanol. Extractive distillation would be an attractive method of effecting the separation of methyl acetate from methanol if agents can be found that (1) will break the methyl acetate-methanol azeotrope and (2) are easy to recover from the methanol, that is, form no azeotrope with methanol and boil sufficiently above methanol to make the separation by rectification possible with only a few theoretical plates.

Extractive distillation typically requires the addition of an equal amount to twice as much extractive agent as the methyl acetate-methanol on each plate in the rectification column. The extractive agent should be heated to about the same temperature as the plate into which it is introduced. Thus extractive distillation imposes an additional heat requirement on the column as well as somewhat larger plates. However this is less than the increase occasioned by the additional agents required in azeotropic distillation.

Another consideration in the selection of the extractive distillation agent is its recovery from the bottoms product. The usual method is by rectification in another column. In order to keep the cost of this operation to a minimum, an appreciable boiling point difference between the compound being separated and the extractive agent is desirable. It is also desirable that the extractive agent be miscible with methanol otherwise it will form a two phase azeotrope with the methanol in the recovery column and some other method of separation will have to be employed.

The breaking of this azeotrope by extractive distillation is a new concept. The closest application of the concept might be the breaking of the ethanol-water azeotrope. J. Schneible, (U.S. Pat. No. 1,469,447) used glycerol; P. V. Smith & C. S. Carlson, (U.S. Pat. No. 2,559,519) employed ethoxyethanol and butoxyethanol for this purpose and W. E. Catterall, (U.S. Pat. No. 2,591,672) reported gasoline as being effective. These are dehydrations and operate more conventionally as a solvent extraction process rather than an extractive distillation.

OBJECTIVE OF THE INVENTION

The object of this invention is to provide a process or method of extractive distillation that will enhance the relative volatility of methyl acetate from methanol in their separation in a rectification column. It is a further object of this invention to identify suitable extractive distillation agents which will eliminate the methyl acetate-methanol binary azeotrope and make possible the production of pure methyl acetate and methanol by rectification. It is a further object of this invention to identify organic compounds which, in addition to the above constraints, are stable, can be separated from methanol by rectification with relatively few plates and can be recycled to the extractive distillation column and reused with little decomposition.

SUMMARY OF THE INVENTION

The objects of this invention are provided by a process for separating methyl acetate from methanol which entails the use of certain oxygenated, nitrogenous and/or sulfur containing organic compounds as the agent in extractive distillation.

DETAILED DESCRIPTION OF THE INVENTION

We have discovered that certain oxygenated, nitrogenous and/or sulfur containing organic compounds, some individually but principally as mixtures, will effectively negate the methyl acetate-methanol azeotrope and permit the separation of pure methyl acetate from methanol by rectification when employed as the agent in extractive distillation. Table I lists the compounds, mixtures and approximate proportions that we have found to be effective. The data in Table I was obtained in a vapor-liquid equilibrium still. In each case, the starting material was the methyl acetate-methanol azeotrope. The ratios are the parts by weight of extractive agent used per part of methyl acetate-methanol azeotrope. The relative volatilities are listed for each of the two ratios employed. The compounds that are effective as extractive distillation agents when used alone are dimethylsulfoxide and dimethylformamide. The compounds which are effective when used in mixtures of two or more components are 1,4-butanediol, 1,5-pentanediol, 1,6-hexanediol, hexylene glycol, diethylene glycol, triethylene glycol, tetraethylene glycol, dipropylene glycol, polyethylene glycol, 3-chloro-1,2-propanediol, diisooctyl phthalate, propylene carbonate and sulfolane.

The two relative volatilities shown in Table I correspond to the two different ratios employed. For example in Table I, one part of dimethylsulfoxide (DMSO) with one part of methyl acetate-methanol azeotrope gives a relative volatility of 3.25, 6/5 parts of DMSO gives 3.38. One half part of DMSO mixed with one half part of 1,4-butanediol with one part of methyl acetate-methanol azeotrope gives a relative volatility of 2.98, 3/5 parts of DMSO plus 3/5 parts of 1,4-butanediol gives 3.01. One third parts of DMSO plus ⅓ parts of propylene glycol plus ⅓ parts of 1,6-hexanediol mixed with one part of methyl acetate-methanol azeotrope gives a relative volatility of 2.86, with 2/5 parts, these three give 2.23. In every example of Table I, the starting material is the methyl acetate-methanol azeotrope which possesses a relative volatility of 1.00.

Several of the compounds and mixtures listed in Table I and whose relative volatility has been determined in the vapor-liquid equilibrium still, were then evaluated in a glass perforated plate rectification column possessing 4.5 theoretical plates. The results are listed in Table II. The methyl acetate-methanol mixture studied contained 15 wt.% methyl acetate, 85 wt.% methanol. The methyl acetate-methanol azeotrope contains 81.3 wt.% methyl acetate, 18.7 wt.% methanol. In every case the feed or bottoms composition contained less than 18.7% methanol and in every case the overhead is richer than 81.3% methyl acetate. Without the extractive agent, the overhead would be the azeotrope, 81.3% methyl acetate. This proves that the extractive agent is negating the azeotrope and makes the rectification proceed as if the azeotrope no longer existed and brings the more volatile component, methyl acetate, out as the overhead. It is our belief that this is the first time that this has been accomplished for any azeotrope.

The data in Table II was obtained in the following manner. The charge designated "blank" was 15% methyl acetate, 85% methanol and after a half hour of operation in the 4.5 theoretical plate column, the relative volatility of the separation between the methyl acetate-methanol azeotrope and methanol was 2.11. The remaining data is for the extractive distillation agents designated. Here we have negated the azeotrope. The temperature of the overhead approaches 52° C., the boiling point of pure methyl acetate at 630 mm. Hg. and the methanol goes to the stillpot with the extractive distillation agent. The designation "R" by the extractive distillation agent means that the same material was recovered and re-used to show its stability in repeated operation. When the methanol-extractive distillation agent mixture taken from the stillpot is redistilled, methanol comes off overhead in the usual way at its normal boiling point, 60.4° C. at 630 mm. Hg.

THE USEFULNESS OF THE INVENTION

The usefulness or utility of this invention can be demonstrated by referring to the data presented in Tables I and II. All of the successful extractive distillation agents show that methyl acetate and methanol can be separated from their binary azeotrope by means of distillation in a rectification column and that the ease of separation as measured by relative volatility is considerable. Without these extractive distillation agents, no improvement above the azeotrope composition will occur in the rectification column.

TABLE I

Extractive Distillation Agents Which Are Effective In Separating Methyl Acetate From Methanol

| Compounds | Ratios | Relative Volatilities | |
| --- | --- | --- | --- |
| Dimethylsulfoxide (DMSO) | 1  6/5 | 3.25 | 3.35 |
| Dimethylformamide (DMFA) | " | 1.55 | 2.24 |
| DMSO, Propylene glycol | (½)$^2$(3/5)$^2$ | 1.93 | 2.52 |
| DMSO, 1,3-Butanediol | " | 3.21 | 2.47 |
| DMSO, 1,4-Butanediol | " | 2.98 | 3.01 |
| DMSO, 1,5-Pentanediol | " | 2.70 | 2.49 |
| DMSO, 1,6-Hexanediol | " | 2.90 | 2.86 |
| DMSO, Hexylene glycol | " | 1.82 | 2.45 |
| DMSO, Diethylene glycol | " | 2.30 | 2.39 |
| DMSO, Dipropylene glycol | " | 3.05 | 2.72 |
| DMSO, Triethylene glycol | " | 2.78 | 2.88 |
| DMSO, Tetraethylene glycol | " | 2.80 | 2.78 |
| DMSO, 3-Chloro-1,2-propanediol | " | 2.36 | 2.06 |
| DMSO, Polyethylene glycol 300 | " | 2.61 | 2.26 |
| DMSO, Diisooctyl phthalate | " | 2.05 | 2.39 |
| DMSO, Propylene carbonate | " | 1.97 | 2.49 |
| DMSO, Sulfolane | " | 2.48 | 2.54 |
| DMSO, Nitrobenzene | " | 1.82 | 1.43 |
| DMSO, Adiponitrile, Sulfolane | (⅓)$^3$(2/5)$^3$ | 1.78 | 1.51 |
| DMSO, Propylene glycol, 1,6-Hexanediol | " | 2.86 | 2.23 |
| DMSO, 1,4-Butanediol, 1,6-Hexanediol | " | 2.63 | 2.48 |
| DMSO, 1,5-Pentanediol, Propylene glycol | " | 2.48 | 2.47 |
| DMSO, 1,5-Pentanediol, 1,4-Butanediol | " | 3.42 | 2.63 |

TABLE I-continued
Extractive Distillation Agents Which Are Effective In Separating Methyl Acetate From Methanol

| Compounds | Ratios | Relative Volatilities | |
|---|---|---|---|
| DMSO, 1,5-Pentanediol, 1,6-Hexanediol | " | 2.57 | 2.45 |
| DMSO, 1,5-Pentanediol, Hexylene glycol | " | 3.05 | 2.28 |
| DMSO, 1,5-Pentanediol, Diethylene glycol | " | 2.43 | 2.47 |
| DMSO, 1,5-Pentanediol, Triethylene glycol | " | 2.84 | 2.39 |
| DMSO, 1,5-Pentanediol, Tetraethylene glycol | " | 2.61 | 2.47 |
| DMSO, 1,5-Pentanediol, Dipropylene glycol | " | 2.39 | 2.23 |
| DMSO, 1,5-Pentanediol, 3-Chloro-1,2-propanediol | " | 2.11 | 2.32 |

TABLE II
Data From Runs Made In Rectification Column

| Compounds | Overhead Temp., °C. | Stillpot Temp., °C. | | Relative Volatility |
|---|---|---|---|---|
| | | Start | After 2 hrs. | |
| Blank | 48.2 | 58.0 | 58.2 | 2.11 |
| DMSO | 57.2 | 60.8 | 103.0 | 7.72 |
| DMSO + Ethylene glycol (R) | 53.2 | 61.6 | 91.0 | 6.62 |
| DMSO + Glycerine + Ethylene glycol (R) | 52.2 | 61.6 | 91.6 | 6.24 |
| DMSO + Glycerine + Diethylene glycol (R) | 51.8 | 62.6 | 87.8 | 5.01 |

Notes:
Mixture Used: 15 wt. % Methyl acetate, 85 wt. % Methanol
(R): Solvents reclaimed and reused
Feed Conditions: Solvents added at 48 ± 2° C. & 20 ml/min.
Boil-up Rate: 10–16 ml/min. Equilibrium in 1 hr.
Ratios: 1:1 or 1:1:1

The data also show that the most attractive agents will operate at a boilup rate low enough to make this a useful and efficient method of recovering high purity methyl acetate from any mixture of these two including the binary minimum azeotrope. The stability of the compounds used and the boiling point difference is such that complete recovery and recycle is obtainable by a simple distillation and the amount required for make-up is small.

WORKING EXAMPLES

Example 1

The methyl acetate-methanol azeotrope is 81.3 wt.% methyl acetate, 18.7 wt.% methanol. Fifty grams of the methyl acetate-methanol azeotrope and fifty grams of DMSO were charged to an Othmer type glass vapor-liquid equilibrium still and refluxed for eleven hours. Analysis of the vapor and liquid by gas chromatography gave vapor 89.9% methyl acetate, 10.1% methanol; liquid of 73.3% methyl acetate, 26.7% methanol. This indicates a relative volatility of 3.25. Ten grams of DMSO were added and refluxing continued for another 13 hours. Analysis indicated a vapor composition of 90.3% methyl acetate, 9.7% methanol, a liquid composition of 73.3% methyl acetate, 26.7% methanol which is a relative volatility of 3.38.

Example 2

Fifty grams of the methyl acetate-methanol azeotrope, 25 grams of DMSO and 25 grams of tetraethylene glycol were charged to the vapor-liquid equilibrium still and refluxed for eleven hours. Analysis indicated a vapor composition of 91.5% methyl acetate, 8.5% methanol, a liquid composition of 79.4% methyl acetate, 20.6% methanol which is a relative volatility of 2.80 Five grams of DMSO and five grams of tetraethylene glycol were added and refluxing continued for another 8 hours. Analysis indicated a vapor composition of 88.1% methyl acetate, 11.9% methanol, a liquid composition of 73.6% methyl acetate, 27.4% methanol which is a relative volatility of 2.78

Example 3

Fifty grams of the methyl acetate-methanol azeotrope, 17 grams of 1,6-hexanediol, 17 grams of DMSO and 17 grams of 1,5-pentanediol were charged to the vapor-liquid equilibrium still and refluxed for eleven hours. Analysis indicated a vapor composition of 86.4% methyl acetate, 13.6% methanol, a liquid composition of 71.2% methyl acetate, 28.8% methanol which is a relative volatility of 2.57. Three grams each of 1,6-hexanediol, DMSO and 1,5-pentanediol were added and refluxing continued for another twelve hours. Analysis indicated a vapor composition of 87.5% methyl acetate, 12.5% methanol, a liquid composition of 74.1% methyl acetate, 25.9% methanol which is a relative volatility of 2.45.

Example 4

A glass perforated plate rectification column was calibrated with ethylbenzene and p-xylene which possesses a relative volatility of 1.06 and found to have 4.5 theoretical plates. A solution of 75 grams of methyl acetate and 425 grams of methanol was placed in the stillpot and heated. When refluxing began, an extractive agent containing pure DMSO was pumped into the column at a rate of 20 ml/min. The temperature of the extractive agent as it entered the column was 48° C. After establishing the feed rate of the extractive agent, the heat input to the methyl acetate and methanol in the stillpot was adjusted to give a total reflux rate of 10–20 ml/min. After one-half hour of operation, the overhead and bottoms samples of approximately two ml. were collected and analysed using gas chromatography. The overhead analysis was 99% methyl acetate, 1% methanol. The bottoms analysis was 8.8% methyl acetate, 91.2% methanol. Using these compositions in the Fenske equation, with the number of theoretical plates in the column being 4,5 gave an average relative volatility of 4.67 for each theoretical plate. After one hour of total operating time, the overhead and bottoms samples were again taken and analysed. The overhead composition was 99.9% methyl acetate, 0.1% methanol and the bottoms composition was 9.2% methyl acetate, 90.8% methanol. This gave an average relative volatility of 7.72 for each theoretical plate. After 1.5 hours of total operating time, the overhead and bottoms samples were again taken and analysed. The overhead composition was 99.9% methyl acetate, 0.1% methanol and the bottoms composition was 7.2% methyl acetate, 92.8% methanol. This gave an average relative volatility of 8.19 for each theoretical plate. After two hours of total operating time, the overhead and bottoms samples were again taken and analysed. The overhead composition was 99.9% methyl acetate, 0.1% methanol and the bottoms composition was 7.2% methyl acetate, 92.8% methanol. This gave an average relative volatility of 8.19.

Example 5

A solution of 75 grams of methyl acetate and 425 grams of methanol was placed in the stillpot of the same column used in example 4 and heat applied. When the refluxing began, an extractive agent of 50% DMSO and 50% ethylene glycol was fed into the top of the column at a feed rate of 20 ml/min. and a temperature of 48° C. After establishing the feed rate of the extractive agent, the heat input to the methyl acetate and methanol in the stillpot was adjusted to give a total reflux rate of 10-20 ml/min. Having established the reflux rate, the column was allowed to operate for one-half hour. After one-half hour of steady operation, overhead and bottoms samples of approximately two ml. were collected and analysed using gas chromatography. The overhead analysis was 99.6% methyl acetate, 0.4% methanol, the bottoms analysis was 8.3% methyl acetate, 91.7% methanol. Using these compositions in the Fenske equation with the number of theoretical plates in the column being 4.5, gave an average relative volatility of 5.81 for each theoretical plate. After one hour of total operation, the overhead composition was 99.7% methyl acetate, 0.3% methanol and the bottoms composition was 4.2% methyl acetate, 95.8% methanol. This gave an average relative volatility of 7.28 for each theoretical plate.

Example 6

A solution of 75 grams of methyl acetate and 425 grams of methanol was placed in the stillpot of the same column used in Example 4 and heat applied. When refluxing began, an extractive agent comprising pure DMSO was fed into the top of the column at a temperature of 48° C. The heat input to stillpot was adjusted to give a total reflux rate of 10-20 l/min. and two hours allowed for the column to reach equilibrium. For the first run the feed rate of the DMSO was 20 ml/min., for the second run it was dropped to 10 ml/min., for the third run it was again dropped to 5 ml/min. and for the forth run it was increased back to the original 20 ml/min. rate. For each run after the first, the DMSO was reclaimed and reused. The following data was obtained:

| Run No. | Feed Rate, ml/min. | Wt % Methyl acetate Overhead | Bottoms | Relative Volatility |
|---|---|---|---|---|
| 1 | 20 | 99.9 | 9.2 | 7.72 |
| 2 | 10 | 99.8 | 8.1 | 6.82 |
| 3 | 5 | 98.9 | 8.2 | 4.65 |
| 4 | 20 | 99.9 | 8.4 | 7.89 |

As the rate of feed of the extractive agent is reduced, the relative volatility declines from 7.72 at 20 ml/min. to 4.65 at 5 ml/min. When the feed rate is restored to 20 ml/min., the relative volatility goes back to 7.89. This shows the importance of using the proper feed rate in extractive distillation.

The nature of the present invention having been described, what we wish to claim as new and useful and secure by Letters Patent is:

1. A method for recovering methyl acetate from a mixture of methyl acetate and methanol which comprises distilling a mixture of methyl acetate and methanol in a rectification column in the presence of an effective amount of an extractive agent, recovering essentially pure methyl acetate as overhead product and obtaining the extractive agent and methanol from the stillpot or reboiler, the extractive agent comprises at least dimethylsulfoxide.

2. The method of claim 1 in which the extractive agent comprises a mixture of dimethylsulfoxide and at least one material from the group consisting of propylene glycol, 1,3-butanediol, 1,4-butanediol, 1,5-pentanediol, 1,6-hexanediol, hexylene glycol, diethylene glycol, triethylene glycol, tetraethylene glycol, dipropylene glycol, polyethylene glycol, 3-chloro-1,2-propanediol, diisooctyl phthalate, propylene carbonate, sulfolane, and adiponitrile.

* * * * *